(12) United States Patent
DelMonego et al.

(10) Patent No.: US 7,562,026 B2
(45) Date of Patent: Jul. 14, 2009

(54) HEALTHCARE PROCEDURE AND RESOURCE SCHEDULING SYSTEM

(75) Inventors: Brian DelMonego, Chester Springs, PA (US); Betty Fink, Bear, DE (US); Gary Grzywacz, Harleysville, PA (US); James Pressler, West Chester, PA (US); Donald Taylor, Downingtown, PA (US); Arnold Teres, Broomall, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 272 days.

(21) Appl. No.: 11/250,702

(22) Filed: Oct. 13, 2005

(65) Prior Publication Data

US 2006/0184943 A1 Aug. 17, 2006

Related U.S. Application Data

(60) Provisional application No. 60/627,376, filed on Nov. 12, 2004.

(51) Int. Cl.
G06Q 10/00 (2006.01)
G06Q 50/00 (2006.01)
A61B 5/00 (2006.01)
G06F 19/00 (2006.01)
G06Q 99/00 (2006.01)

(52) U.S. Cl. .................. 705/2; 705/3; 705/52
(58) Field of Classification Search ............ 705/2, 705/3, 4, 52
See application file for complete search history.

(56) References Cited

U.S. PATENT DOCUMENTS

| 5,184,314 | A | * | 2/1993 | Kelly et al. ............... 708/131 |
|---|---|---|---|---|
| 5,291,399 | A | * | 3/1994 | Chaco ............................ 705/3 |
| 5,822,544 | A | * | 10/1998 | Chaco et al. ................... 705/2 |
| 6,401,055 | B1 | * | 6/2002 | Petta ......................... 702/182 |
| 6,671,563 | B1 | * | 12/2003 | Engelson et al. ............... 700/2 |
| 6,714,913 | B2 | * | 3/2004 | Brandt et al. ................... 705/2 |
| 7,158,030 | B2 | * | 1/2007 | Chung .................... 340/572.1 |
| 2003/0036927 | A1 | | 2/2003 | Bowen |
| 2003/0050797 | A1 | | 3/2003 | Brandt et al. |
| 2003/0050821 | A1 | | 3/2003 | Brandt et al. |
| 2004/0152952 | A1 | | 8/2004 | Gotlib et al. |
| 2004/0249676 | A1 | | 12/2004 | Marshall et al. |
| 2004/0260576 | A1 | | 12/2004 | Wang et al. |
| 2004/0261063 | A1 | | 12/2004 | Wang et al. |
| 2005/0060211 | A1 | | 3/2005 | Xiao et al. |

\* cited by examiner

*Primary Examiner*—Gerald J. O'Connor
*Assistant Examiner*—Amber L Altschul
(74) *Attorney, Agent, or Firm*—Alexander J. Burke

(57) ABSTRACT

A User Interface system provides a physician with a user-friendly overview of operational and resource information of a Radiology Information System (RIS) and uses rules and hospital knowledge to find and filter RIS information to provide information facilitating making a particular decision. A radiology resource monitoring system comprises at least one repository including, data identifying scheduled procedures, data identifying room and equipment availability and data identifying clinician availability. A patient tracking unit monitors patient status including progress of patient procedures and patient arrival. An information management processor updates a task schedule of a worker in response to a change in patient status indicated by the tracking unit and in response to data derived from the at least one repository.

17 Claims, 4 Drawing Sheets

FIGURE 3

| Field | Characters | Signals Utilized |
|---|---|---|
| Patient Name | | |
| | | |
| | | |
| | | |
| | | |
| | | |
| | | |
| | | |

303  305  308

HEALTHCARE PROCEDURE AND RESOURCE SCHEDULING SYSTEM

This is a non-provisional application of provisional application Ser. No. 60/627,376 by Brian DelMonego et al. filed Nov. 12, 2004.

FIELD OF THE INVENTION

This invention concerns a system for monitoring radiology resources and patient status and tracking patients and progress of patient procedures.

BACKGROUND OF THE INVENTION

An existing Radiology Information System (RIS) application typically require a user to switch between image windows, images or even displays when a user desires to view different information. For instance when a clinician (e.g., a nurse, technician or physician) desires to know the capacity of available radiology resources on a specific day the clinician may need to switch to an image presenting a resource plan for this day. Specifically, in order to see patient room and equipment utilization a clinician needs to switch to another image window and to remember the personnel resources shown in the previous window. In bigger healthcare enterprises, it is desirable for a user to be able to view one image and determine operation and activity status of different sections within an Imaging Department, for example. It is also desirable for a user to be able to redirect patients from one overloaded room to another room that is not overloaded. A system according to invention principles addresses these deficiencies and related problems.

SUMMARY OF THE INVENTION

The inventors have advantageously recognized the need for a more user friendly overview of RIS information that provides one image for use in determining operation and activity status as well as personnel and equipment resource availability and automatically adaptively compensates for an unscheduled delay in an activity and facilitates re-direction of patients to optimize resource usage. A radiology resource monitoring system comprises at least one repository including, data identifying scheduled procedures, data identifying room and equipment availability and data identifying clinician availability. A patient tracking unit monitors patient status including progress of patient procedures and patient arrival. An information management processor updates a task schedule of a worker in response to a change in patient status indicated by the tracking unit and in response to data derived from the at least one repository.

BRIEF DESCRIPTION OF THE DRAWING

FIG. 3 shows a display image presenting additional information items together with the resource and status monitoring information in a composite single display image, according to invention principles.

DETAILED DESCRIPTION OF INVENTION

Figure 1:
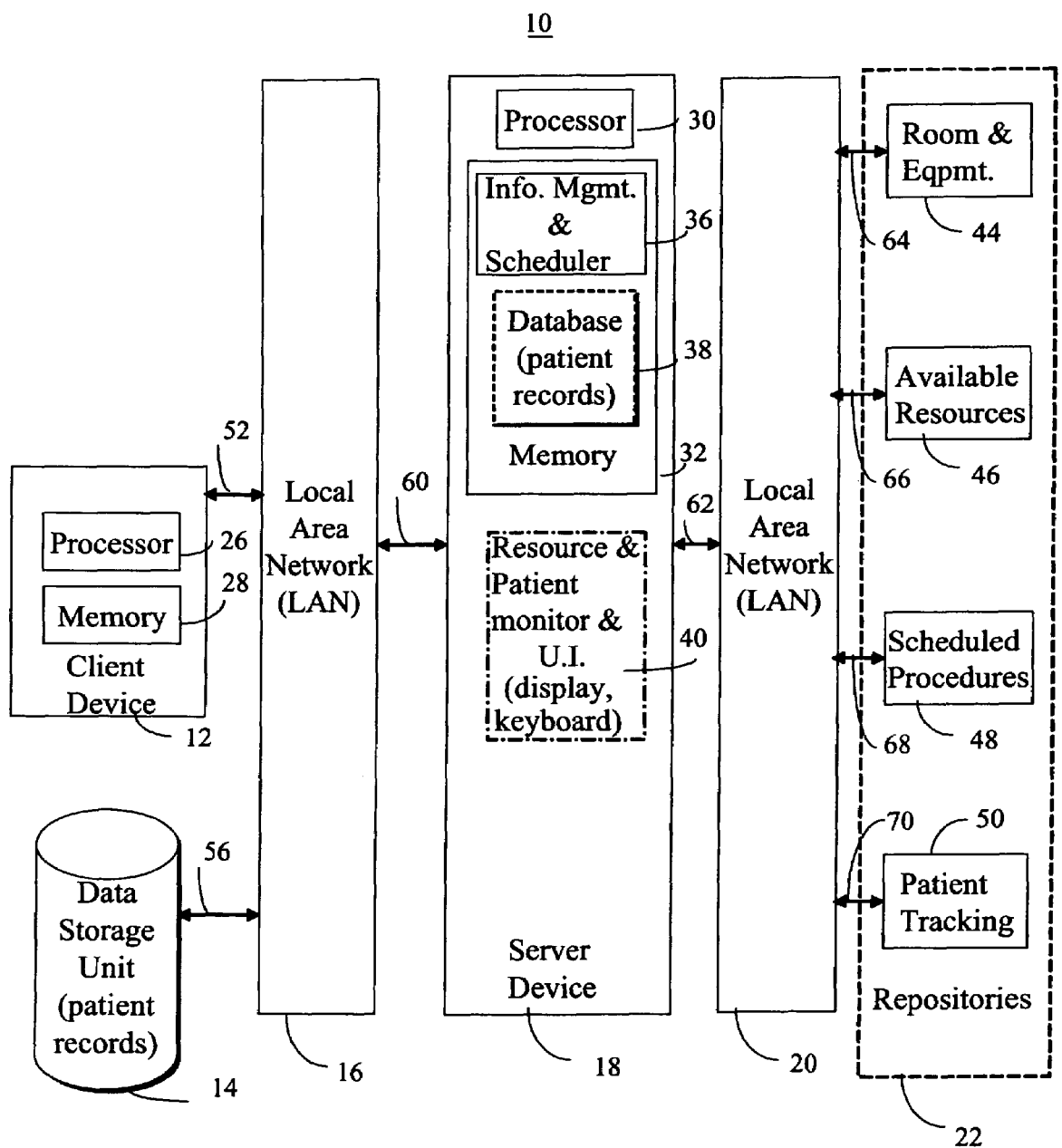
FIG. 1 shows a networked radiology information system providing a resource monitoring function and user interface, according to invention principles.

FIG. 1 shows a networked radiology information system 10 providing a resource monitoring function and user interface. The system employs user interface software and adaptive processing software incorporating functions adaptively modified in response to previous results. The resource monitoring function and user interface are connected to an existing Radiology Information Systems (RIS) of a hospital, for example. The user interface provides a clinician with a user-friendly overview of the most significant information derived from a RIS that supports the making of a particular decision by a physician. The adaptive processing software implements rules and operates using hospital data and knowledge in finding and filtering RIS data to provide information facilitating the making of a particular decision by a physician. As an example, an Imaging Department is informed by an Emergency Room that a patient needs to have an emergency procedure. The emergency department needs to know when a particular imaging resource (e.g., a medical device, supplies or personnel) is available. A radiology worker employs the resource monitoring system and user interface to generate a display image for viewing showing a schedule of resources (a "white board") indicating their status, duration of use, priority of use, and time (and date) of availability. The radiology worker employs the display image showing the schedule of resources to determine a first available time that the emergency procedure may be performed for the patient. Thereby, Emergency Room personnel advantageously do not have to wait for radiology staff to locate someone to provide them the needed availability information.

In another example of operation, a CT (Computerized Tomography) technologist has two (first and second) patients that are ready and waiting to have procedures performed. A procedure to be performed for a first patient requires that a radiologist is available. The CT technologist examines the display image showing a schedule of resources to see if the radiologist has started a procedure for another different patient and if so, determines how long the radiologist has been involved in order to decide on which of the first and second patients is to be treated first. This saves the CT technologist time that would otherwise be involved in tracking down the radiologist and perhaps starting treatment of the first and second patients in the least efficient order.

If a next patient is already waiting for a procedure but a room and equipment are not yet available, the display image showing a schedule of resources gives an approximate time indication of how long it is likely to be before the radiologist completes his current assignment. If the radiologist is delayed, the resource monitoring system calculates for individual patients an approximate delay time. Thereby, an individual patient is informed of an approximate likely delay. If the assignment takes more time than originally allocated, the resource monitoring function adds a short time period (for example 5 minutes) to the calculated approximate likely delay for individual patients. The calculated approximate likely delay time for individual patients is calculated for individual rooms, physicians and items of equipment and the delay times are presented in the display image showing the schedule of resources. In larger healthcare organizations, if a delay is significant, the resource monitoring system provides candidate scheduling solutions to problems that occur. For example, if a room is not yet free for a procedure, the resource monitoring system suggests a room that may be used for that procedure. The resource monitoring system also suggests another physician or other healthcare worker that is already available, likely to be available sooner than the assigned worker or is engaged in duties that are of lower priority than those of the assigned worker.

An executable application as used herein comprises code or machine readable instruction for implementing predetermined functions including those of an operating system, healthcare (e.g., radiology) information system or other information processing system, for example, in response user command or input. An executable procedure is a segment of code (machine readable instruction), sub-routine, or other distinct section of code or portion of an executable application for performing one or more particular processes and may include performing operations on received input parameters (or in response to received input parameters) and provide resulting output parameters. A processor as used herein is a device and/or set of machine-readable instructions for performing tasks. A processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A display processor or generator is a known element comprising electronic circuitry or software or a combination of both for generating display images or portions thereof. A user interface comprises one or more display images enabling user interaction with a processor or other device and functions for associated data processing.

FIG. 1 shows a networked radiology information system 10 providing a resource monitoring function and associated user interface 40. Radiology information system 10 includes a client device 12, a data storage unit 14, a first local area network (LAN) 16, a server device 18, a second local area network (LAN) 20, and repositories 22. Repositories 22 may comprise one repository (e.g., a database) or multiple repositories. The client device 12, e.g., a radiology image viewing or other workstation, includes processor 26 and memory unit 28 and may comprise a personal computer, for example. The Radiology information system 10 is used by a healthcare provider that is responsible for providing radiological services within a hospital or as a separate facility. Although the system is described in the context of a radiology department, this is exemplary only. The system is also applicable in other hospital departments (e.g. cardiology, etc.). Examples of healthcare providers include, without limitation, a hospital, a nursing home, an assisted living care arrangement, a home health care arrangement, a hospice arrangement, a critical care arrangement, a health care clinic, a physical therapy clinic, a chiropractic clinic, and a dental office. Examples of the people being serviced by the healthcare provider include, without limitation, a patient, a resident, and a client.

Server device 18 includes resource monitoring system and associated user interface 40, processor 30, a memory unit 32 including information management, scheduling and workflow system 36 (including a decision engine) and a database 38 containing patient records including medical data identifying treatments previously received by a patient. Resource monitoring and user interface system 40 (which may also reside in client device 12) includes an input device that permits a user to perform data and command entry and input information and an output device that provides a user a display image showing a schedule of resources. The display image indicates the status of resources, their duration of use, priority of use, and time (and date) of availability. The system 40 input device is a keyboard and mouse, but also may be a touch screen or a microphone with a voice recognition program, or a telephone voice response system for example. The output device, as an alternative (or in addition to) a display, may be a speaker, for example. The output device provides information to the user responsive to the input device receiving information from the user or responsive to other activity by client device 12. For example, a display presents information responsive to the user entering information via a keyboard.

Resource monitoring system 40 in conjunction with information management unit 36, automatically acquires, collates and presents RIS information in response to user command based on predetermined rules and instruction stored in memory 32. The manual compilation of RIS information, in contrast, typically requires an expert (e.g., a physician, radiologist) with specific hospital knowledge. Resource monitoring system 40 in conjunction with information management unit 36 acquires and collates RIS information from repositories 22 (which may comprise one or more databases, for example). Repositories 22 include, repository 44 containing room and equipment availability information, repository 46 identifying resources and their current and future availability, repository 48 including information indicating scheduled treatment procedures and repository 50 containing information indicating current and future patient location.

Resource monitoring system 40 in conjunction with information management unit 36, employs information acquired from repositories 22 to calculate approximate likely, room, physician and equipment availability times and any associated delay times for procedures to be performed for individual patients. Resource monitoring system 40 in conjunction with information management unit 36 calculates delay using predetermined stored information (e.g., in database 38) indicating typical duration times of different types of procedures and duties. This predetermined information is employed together with schedule data derived from unit 36 identifying current and future types of procedures and duties being performed by particular healthcare workers or that are scheduled to be performed by particular workers in particular rooms using particular medical equipment. System 40 uses the predetermined information and schedule data to arithmetically estimate times of completion of particular procedures and duties, start times of procedures and duties and any associated delays derived from room, worker or equipment unavailability, schedule conflicts or unscheduled interruptions. Such unscheduled interruptions include, worker illness or re-assignment, equipment failure, patient delay resulting from failure to meet an appointment or due to an adverse reaction or room unavailability due to an unscheduled maintenance requirement, for example.

System 40 provides a display image including user desired information in response to predetermined or default user interface configuration information or in response to user command via one or more displayed information selection menus. The display image includes data indicating any combination of, the status of resources, their duration of use, priority of use, and time (and date) of availability as well as likely availability times and any associated delay times for individual patients as well as for individual rooms, physicians and items of equipment. System 40 provides the display image that automatically adaptively compensates for an unscheduled delay in an activity and facilitates switching patients to optimize resource usage and includes user desired information by compilation of multiple sets of data derived from disparate sources including repositories 22. The display image provides an advantageous single composite image (and multiple images where the quantity of information necessitates) enabling optimization of radiology workflow and improved productivity and worker and equipment utilization.

The display image advantageously addresses existing system deficiencies. Specifically, in existing systems, workers typically rely on a printed schedule lacking connection to current status updates or manually enter information on a white board, for example. As a result, if a schedule change occurs, the printed schedule contains incorrect, out of date information. Further, in existing systems a user needs to access (involving switching between, and remembering data from) multiple different executable applications (and associated images) to determine activities and status of activities in a radiology department, for example. The need to manually remember often large quantities of information between different images, results in errors in interpretation of information from the different images as well as in error resulting from missing pertinent information. This lack of automation results in a planning physician failing to obtain an operations overview and to be uncertain of scheduling and resource availability status. This reduces productivity, since a user has to manually look in multiple places for information resulting in rooms, personnel and equipment being under utilized. Further, patient hospital stays and outpatient visits are increased due to delay.

In contrast the display image provided by system 40 is automatically populated with information derived from a RIS by system 40 operating with unit 36 without manual data entry to provide an overall view of an imaging department activities and operations for a day (or other time period), for example. Thereby, patients and medical team members are provided with information indicating an approximate time a procedure is likely to take and also a time at which a subsequent procedure is likely to be completed. Consequently, it can be determined how long a patient may have to wait.

In operation, a scheduling function in unit 36 in RIS 10 schedules a patient to receive a procedure. RIS 10 is aware of the resources that are needed and the time periods for which they are needed for the scheduled procedure. Resource and procedure scheduling information, as well as patient tracking, resource availability and room and equipment scheduling information is stored in RIS repositories 22. This information is processed by system 40 to provide a display image indicating procedures scheduled for the current day together with the status of needed resources, their duration of use, priority of use, and time (and date) of availability. System 40 automatically tracks an individual procedure by progress of individual component steps of the procedure (e.g., availability of equipment, room and personnel, room preparation, equipment preparation, patient location, patient preparation, progress of portions of the procedure, documentation) and this progress information is used to automatically update the status display image. For example, if a system 40 patient tracking function automatically locates a patient in a room associated with a worker assigned to perform duties of a scheduled procedure during the scheduled time of the procedure, for example, system 40 updates the display image to indicate the examination room (or procedure room) associated with this scheduled procedure or worker is being utilized and is unavailable for a specific period. System 40 automatically updates status information concerning this procedure and associated resources within repositories 22. Further, in response to system 40 tracking an assigned Radiologist to the examination room to begin the procedure, system 40 updates the display image and associated status information in repositories 22 to indicate that he is not available.

The system 40 user interface is used in conjunction with a workflow engine in unit 36 to optimise Radiology department workflow. A merging and rendering processor in system 40 processes acquired data to provide a single composite display image window incorporating pertinent information supporting the workflow operation. The radiology department workflow optimises resource utilization, monitors rooms as well as healthcare workers, patients and equipment usage. Thereby, at a glance a user determines what resources are currently available and how an emergency procedure may be accommodated, for example. Also, a patient waiting for a particular Radiologist for a procedure or to ask a question, may be directed to another Radiologist using the composite display image. This improves patient care by reducing patient wait times and by keeping the patient informed whereby if a patient is waiting to have a procedure done, a worker can see how long the patient has been waiting and keep the patient informed of the status of the procedure schedule.

Figure 2:
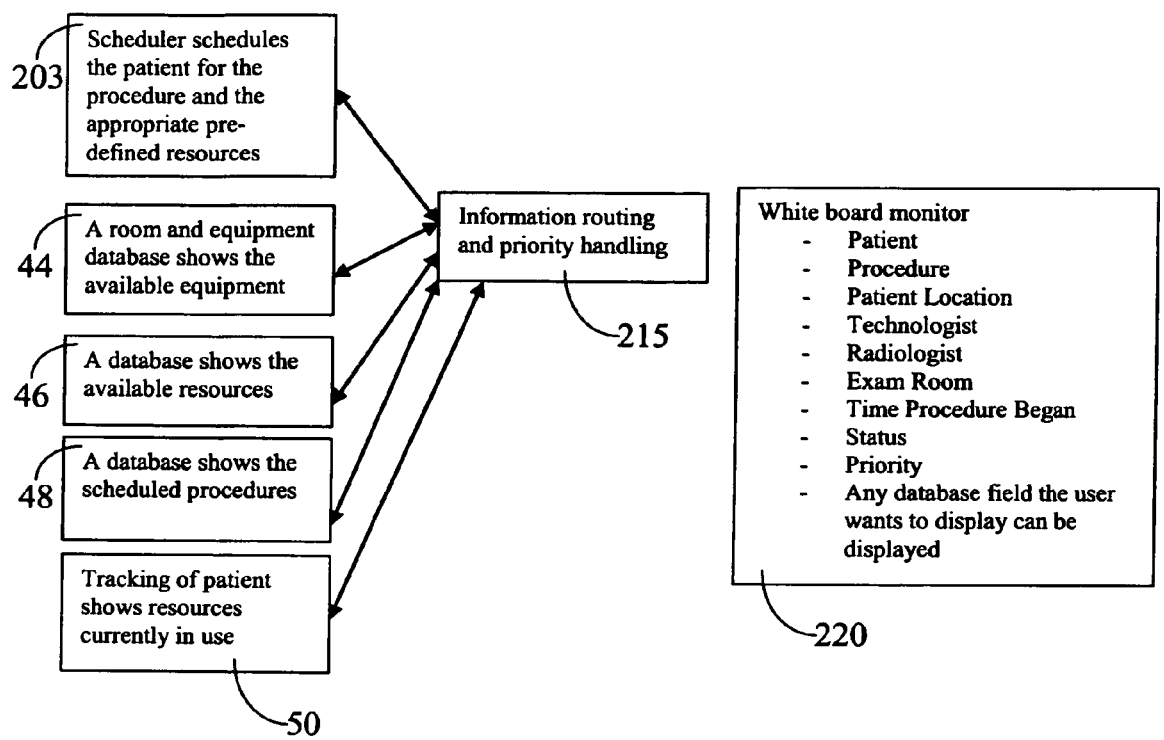
FIG. 2 shows data flow and interaction in the networked radiology information system of FIG. 1, according to invention principles.

FIG. 2 shows data flow and interaction directed by system 40 in conjunction with unit 36 in the networked radiology information system 10 of FIG. 1. A scheduler in unit 36 schedules (203) a patient for a procedure using appropriate resources and updates repositories 22 including room and equipment repository 44, resource availability repository 46, scheduled treatment procedures repository 48 and patient and resource location tracking repository 50. Unit 40 routes and prioritizes information (215) and processes information acquired from repositories 22 and user data entry to provide a composite display image (220) indicating procedures scheduled for the current day together with the status of needed resources, their duration of use, priority of use, and time (and date) of availability. The display images identifies an individual patient, the location of the patient, a procedure to be received by the patient, healthcare workers associated with the procedure, a room to be used as well as the start time and duration of the procedure and its status and priority. Other data fields are displayed as selected by a user via configuration menus provided by system 40 during a configuration operation.

FIG. 3 shows a display image area format for presenting additional information items together with the resource and status monitoring information in a composite single display image. The additional information associates text in column 305 and signals utilized (including, for example, personnel or equipment tracking signals from RFID tag tracking, global positioning, other tag location, priority signals, status signals) in column 308 with corresponding individual patients identified in column 303. Similarly, equipment and physician tracking signal information may also be presented.

Figure 4:
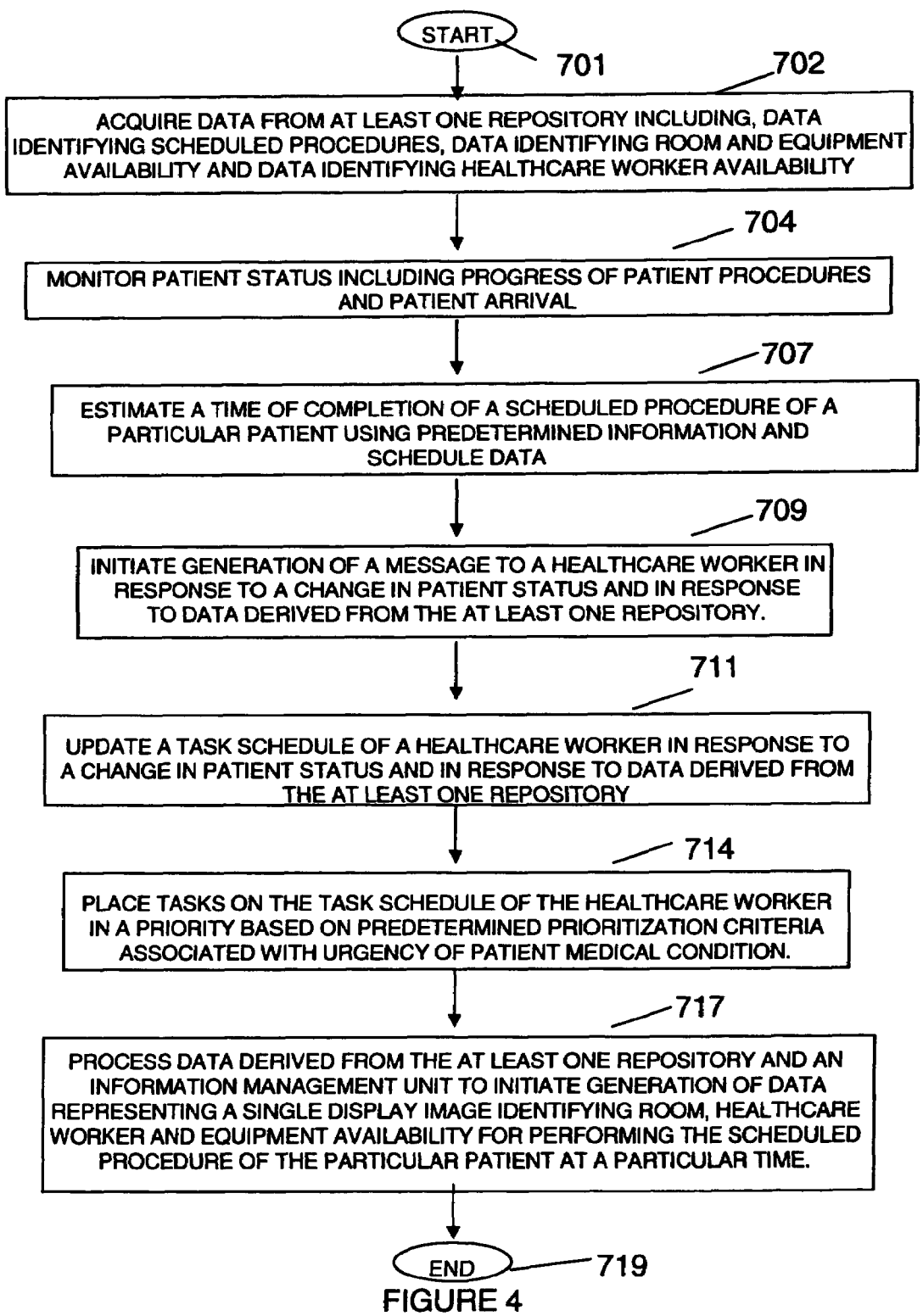
FIG. 4 shows a flowchart of a process employed by a resource monitoring system, according to invention principles.

FIG. 4 shows a flowchart of a process employed by resource monitoring system 40 and information management unit 36. In step 702 following the start at step 701, system 40 and unit 36 acquire data from repositories 22 including, data identifying scheduled procedures, data identifying room and equipment availability and data identifying healthcare worker availability. Repositories 22 contain data indicating patient location, patient identification information and medical records, a time a procedure was started, procedure status and procedure priority, for example. In step 704 a tracking unit in information management unit 36 monitors patient status including progress of patient procedures and patient arrival and in step 707 unit 36 estimates a time of completion of a scheduled procedure of a particular patient using predetermined information and schedule data. Information management unit 36 estimates the time of completion of the scheduled procedure of the particular patient including a delay associated with room, worker or equipment unavailability and uses predetermined information and schedule data to estimate start times of procedures and healthcare worker duties. Also, the tracking unit monitors patient location, healthcare worker location and medical (and other) equipment location. The tracking unit monitors patient location based on data from an RFID tag, another tag or global positioning or other positioning detection.

Information management unit 36 in step 709 initiates generation of a message to a healthcare worker in response to a detected change in patient status indicated by the tracking unit and in response to the data derived from repositories 22. In step 711, information management unit 36 updates a task schedule of a healthcare worker in response to a change in patient status indicated by the tracking unit and in response to data derived from repositories 22. Information management unit 36 in step 714 places tasks on the task schedule of the healthcare worker with a priority based on predetermined prioritization criteria associated with urgency of patient medical condition. System 40, in step 717, processes data derived from repositories 22 and information management unit 36 and initiates generation of data representing a single display image identifying room, healthcare worker and equipment availability for performing the scheduled procedure of the particular patient at a particular time. The single display image is automatically populated with information derived from repositories 22 and information management unit 36 without manual data entry to provide an overall view of activities occurring in a particular time period including information indicating an approximate time duration that a procedure is likely to take. The included information indicates a time at which a subsequent procedure is likely to be completed. The process of FIG. 4 terminates at step 719.

In exemplary operation of system 10, a patient is scheduled for an Angiography examination for the current day. A display image provided by system 40 and unit 36 indicates a time slot for the patient based on the time that the patient is scheduled for the examination. When a healthcare worker logs into RIS system 10, the system indicates the worker as being available via an indication in a display image presenting an overall view of activities and the status of activities and resources in system 10. When the patient arrives the display image indicates (e.g., by flashing, a flag or other indication) that the patient has arrived. The display provides the indication until either a worker acknowledges the arrival of the patient or the patient is introduced to the Angiography section of the department.

The display image provided by unit 40 is updated by units 36 and 40 as the Angiography procedure progresses and if the completion of the procedure is delayed and occupies a room and radiology resources longer than a scheduled duration, the display image indicates the occupied resources are unavailable. The delay triggers unit 36 to generate a message to a nursing station associated in a database with a second patient (if the next patient is an inpatient) for which the occupied resources were allocated for subsequent use. The message alerts the nursing station to defer conveying the second patient to the Radiology department until a further message is received. If the second patient is an outpatient, unit 36 sends a message to a reception desk indicating the delay, so that the second patient can be informed. When the current procedure is tracked by unit 36 to an End Procedure step, unit 36 sends a message to the second patient nursing station (if the next patient is an inpatient) indicating the second patient is to brought to the Radiology department. A message is also sent to a transport group to initiate bringing the second patient to the Radiology department. If the second patient is an outpatient, unit 36 sends a message to a reception desk indicating the radiology department is ready to receive the second patient.

In another example involving a large hospital, twenty three patients are waiting for different examinations and procedures. Rooms are already occupied and the first six patients are examined. Units 36 and 40 automatically assign temporary activities for the remaining seventeen patients comprising assigning provisory rooms and assistance till a physician examines them. Units 36 and 40 automatically provide schedule update information in the display image in response to delay, indicating how long it is likely to be before a patient examination is to occur The schedule update is provided directly to an individual patient via the display image generated by unit 40 or is provided indirectly to an individual patient via healthcare worker access to the display image.

Returning to the FIG. 1 system, server device 18 may be implemented as a personal computer or a workstation. Database 38 provides a location for storing patient treatment records and other patient records (e.g., financial records) and data storage unit 14 provides an alternate store for patient records, as well as other information in system 10. The information in data storage unit 14, database 38, unit 36 and system 40 is accessed by multiple users from multiple client devices. Patient records in data storage unit 14 include information related to a patient including, without limitation, biographical, financial, clinical, workflow, care plan and patient encounter (visit) related information.

The first local area network (LAN) 16 (FIG. 1) provides a communication network among the client device 12, the data storage unit 14 and the server device 18. The second local area network (LAN) 20 provides a communication network between the server device 18 and repositories 22. The first LAN 16 and the second LAN 20 may be the same or different LANs, depending on the particular network configuration and the particular communication protocols implemented. Alternatively, one or both of the first LAN 16 and the second LAN 20 may be implemented as a wide area network (WAN).

The communication paths 52, 56, 60, 62, 64, 66, 68 and 70 permit the various elements, shown in FIG. 1, to communicate with the first LAN 16 or the second LAN 20. Each of the communication paths 52, 56, 60, 62, 64, 66, 68 and 70 are preferably adapted to use one or more data formats, otherwise called protocols, depending on the type and/or configuration of the various elements in the Radiology information systems 10. Examples of the information system data formats include, without limitation, an RS232 protocol, an Ethernet protocol, a Medical Interface Bus (MIB) compatible protocol, DICOM protocol, an Internet Protocol (I.P.) data format, a local area network (LAN) protocol, a wide area network (WAN) protocol, an IEEE bus compatible protocol, and a Health Level Seven (HL7) protocol.

The system, user interface image and processes presented in FIGS. 1-4 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, any of the functions provided by the system of FIG. 1 and process of FIG. 4 may be implemented in hardware, software or a combination of both. The resource monitoring system and display image presents an overall view of activities of an enterprise, showing a schedule of resources indicating their status, duration of use, priority of use, and time (and date) of availability that adaptively compensates for an unscheduled delay in an activity.

What is claimed is:

1. An automated radiology resource monitoring system compensating for unscheduled delay, comprising:
   at least one repository including,
      data identifying scheduled procedures,
      data identifying room and equipment availability and
      data identifying healthcare worker availability;
   a tracking unit, electrically coupled to said at least one repository, for monitoring patient status including progress of currently occurring patient procedures and arrival of patients scheduled for a patient procedure;
   an information management processor, electrically coupled to said tracking unit, for updating a task schedule of a healthcare worker in response to a change in patient status indicated by said tracking unit and in response to data derived from said at least one repository and for adaptively compensating for an unscheduled delay in a currently scheduled patient procedure by arithmetically estimating times of completion of procedures and duties based on,
      predetermined duration times of corresponding procedures and duties and
      delays associated with room, worker or equipment availability, by providing information to a user supporting updating a patient schedule and re-directing a patient in response to a candidate schedule; and
   a display processor, electrically coupled to said tracking unit and said information management processor, for initiating display of a single composite image identifying progress of currently occurring patient procedures, availability of particular equipment, room, and healthcare worker for performing a procedure for a particular patient at a particular time, and associated delay times for a particular patient using particular equipment, room, and healthcare worker, in response to data derived from said tracking unit and said information processor.

2. A system according to claim 1, wherein
   said information management processor generates messages for communication to healthcare workers for re-directing said patient in response to said candidate schedule and
   said information management processor initiates generation of a message to a healthcare worker in response to said change in patient status indicated by said tracking unit and in response to said data derived from said at least one repository.

3. A system according to claim 1, wherein
   said information management processor places tasks on said task schedule of said healthcare worker in a priority based on predetermined prioritization criteria associated with urgency of patient medical condition.

4. A system according to claim 1, wherein
   said at least one repository contains data indicating at least three of, (a) patient location, (b) patient identification information and medical records, (c) a time a procedure was started, (d) procedure status and (e) procedure priority.

5. A system according to claim 1, wherein
   said tracking unit monitors patient location based on data from at least one of, (a) an RFLD tag, (b) another tag and (c) global or other positioning detection.

6. A system according to claim 1, wherein
   said tracking unit monitors at least one of, (a) patient location, (b) healthcare worker location and (c) equipment location.

7. An automated radiology resource monitoring system compensating for unscheduled delay, comprising:
   at least one repository including,
      data identifying scheduled procedures,
      data identifying room and equipment availability and
      data identifying healthcare worker availability;
   a tracking unit, electrically coupled to said at least one repository, for monitoring patient status including progress of currently occurring patient procedures and arrival of patients scheduled for a patient procedure; and
   a display processor, electrically coupled to said tracking unit for initiating display of a single composite image identifying progress of currently occurring patient procedures, availability of particular equipment, room, and healthcare worker for performing a procedure for a particular patient at a particular time, and associated delay times for a particular patient using particular equipment, room, and healthcare worker and information in said single display image is automatically generated in response to adaptively compensating for an unscheduled delay in availability of a currently scheduled patient procedure by arithmetically estimating times of completion of procedures and duties based on,
      predetermined duration times of corresponding procedures and duties and
      delays associated with room, worker or equipment availability, by providing information to a user.

8. A system according to claim 7, wherein
   said single display image is automatically populated with information derived from said at least one repository and said tracking unit without manual data entry to provide an overall view of activities occurring in a particular time period including information indicating an approximate time duration a procedure is likely to take.

9. A system according to claim 8, wherein
   the included information indicates a time at which a subsequent procedure is likely to be completed.

10. A system according to claim 7, including
    an information management processor for updating a task schedule of a healthcare worker in response to a change in patient status indicated by said tracking unit and in response to data derived from said at least one repository.

11. A system according to claim 10, wherein
    said information management processor initiates generation of a message to a healthcare worker in response to said change in patient status indicated by said tracking unit and in response to said data derived from said at least one repository.

12. A system according to claim 10, wherein
    said information management processor places tasks on said task schedule of said healthcare worker in a priority based on predetermined prioritization criteria associated with urgency of patient medical condition.

13. A system according to claim 8, wherein
    said at least one repository contains data indicating at least three of, (a) patient location, (b) patient identification information and medical record, (c) a time a procedure was started, (d) procedure status and (e) procedure priority.

14. A system according to claim 7, wherein
    said tracking unit monitors at least two of, (a) patient location, (b) healthcare worker location and (c) equipment location.

15. An automated radiology resource monitoring system compensating for unscheduled delay, comprising:
    at least one repository including,
       data identifying scheduled procedures
       data identifying room and equipment availability and data identifying healthcare worker availability;

a tracking unit, electrically coupled to said at least one repository, for monitoring patient status including progress of currently occurring patient procedures and arrival of patients scheduled for a patient procedure;

an information management unit, electrically coupled to said at least one repository, for monitoring patient status including progress of currently occurring patient procedures and arrival of patients scheduled for a patient procedure and using predetermined information and schedule data to estimate a time of completion of a scheduled procedure of a particular patient and adaptively compensating for an unscheduled delay in a patient procedure scheduled for a subsequent patient by arithmetically estimating times of completion of procedures and duties based on, predetermined duration times of corresponding procedures and duties and delays associated with room, worker or equipment availability and for generating messages for communication to healthcare workers for re-directing said patient in response to the unscheduled delay; and a display processor, electrically coupled to said tracking unit and said information management unit, for initiating display of a single composite image identifying progress of currently occurring patient procedures, availability of particular equipment, room, and healthcare worker for performing a procedure for a particular patient at a particular time, an overview of patient procedures occurring during a particular user selected time period including a time estimate at which a particular procedure will be completed, and at least one generated message in response to data derived from said tracking unit and said information processor.

16. A system according to claim 15, wherein said information management unit adaptively compensates for an unscheduled delay in a patient procedure scheduled for and associated with a patient currently undergoing a patient procedure; and said information management unit estimates said time of completion of said scheduled procedure of said particular patient including a delay associated with room, worker or equipment unavailability.

17. A system according to claim 16, wherein said information management unit uses predetermined information and schedule data to estimate start times of procedures and healthcare worker duties.

\* \* \* \* \*